US00PP25370P2

(12) United States Plant Patent
Eveleens

(10) Patent No.: US PP25,370 P2
(45) Date of Patent: Mar. 24, 2015

(54) ***ALSTROEMERIA* PLANT NAMED 'TESANTARC'**

(50) Latin Name: *Alstroemeria hybrida*
Varietal Denomination: Tesantarc

(71) Applicant: Peter Eveleens, Aalsmeer (NL)

(72) Inventor: Peter Eveleens, Aalsmeer (NL)

(73) Assignee: VoF Hortipartners, Heerhugowaard (NL)

( * ) Notice: Subject to any disclaimer, the term of this patent is extended or adjusted under 35 U.S.C. 154(b) by 60 days.

(21) Appl. No.: 13/986,781

(22) Filed: Jun. 4, 2013

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Kent L Bell
(74) *Attorney, Agent, or Firm* — C. A. Whealy

(57) ABSTRACT

A new and distinct cultivar of *Alstroemeria* plant named 'Tesantarc', characterized by its upright, somewhat outwardly spreading and uniformly mounded plant habit; sturdy and strong plant form; moderately vigorous growth habit; freely branching habit and relatively short internodes; dense and bushy appearance; large and numerous white-colored flowers with dark red-colored stripes and held above the foliar plane on relatively short flower pedicels; and good garden performance.

1 Drawing Sheet

Botanical designation: *Alstroemeria hybrida.*
Cultivar denomination: 'TESANTARC'.

BACKGROUND OF THE INVENTION

The present invention relates to a new and distinct cultivar of *Alstroemeria* plant, botanically known as *Alstroemeria hybrida*, grown typically as a potted garden *Alstroemeria*, and hereinafter referred to by the name 'Tesantarc'.

The new *Alstroemeria* plant is a product of a planned breeding program conducted by the Inventor in Heerhugowaard, The Netherlands. The objective of the breeding program is to create new freely-flowering potted garden *Alstroemeria* plants with uniform plant habit and attractive flower coloration.

The new *Alstroemeria* plant originated from a cross-pollination made by the Inventor in Heerhugowaard, The Netherlands in April, 2006 of a proprietary selection of *Alstroemeria hybrida* identified as code number Pa6028x002, not patented, as the female, or seed, parent with a proprietary selection of *Alstroemeria* hybrida identified as code number Pb6903x035, not patented, as the male, or pollen, parent. The new *Alstroemeria* plant was discovered and selected by the Inventor as a single flowering plant from within the progeny of the stated cross-pollination in a controlled greenhouse environment in Heerhugowaard, The Netherlands in April, 2007.

Asexual reproduction of the new *Alstroemeria* plant by rhizome divisions in a controlled greenhouse environment in Heerhugowaard, The Netherlands since September, 2007 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tesantarc'. These characteristics in combination distinguish 'Tesantarc' as a new and distinct *Alstroemeria* plant:

1. Upright, somewhat outwardly spreading and uniformly mounded plant habit.
2. Sturdy and strong plant form; moderately vigorous growth habit.
3. Freely branching habit and relatively short internodes; dense and bushy appearance.
4. Large and numerous white-colored flowers with dark red-colored stripes and held above the foliar plane on relatively short flower pedicels.
5. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* have broader leaves than plants of the female parent selection.
2. Plants of the new *Alstroemeria* and the female parent selection in flower color as plants of the female parent selection have pink-colored flowers with light yellow-colored centers.

Plants of the new *Alstroemeria* can be compared to plants of the male parent selection. Plants of the new *Alstroemeria* differ from plants of the male parent selection in the following characteristics:

1. Plants of the new *Alstroemeria* have broader leaves than plants of the male parent selection.
2. Plants of the new *Alstroemeria* and the male parent selection in flower color as plants of the male parent selection have white-colored flowers without stripes.

Plants of the new *Alstroemeria* can be compared to plants of the *Alstroemeria hybrida* 'Tescreda Improved', disclosed in U.S. Plant Pat. No. 24,127. In side-by-side comparisons, plants of the new *Alstroemeria* differ primarily from plants of 'Tescreda Improved' in the following characteristics:

1. Plants of the new *Alstroemeria* have broader leaves than plants of 'Tescreda Improved'.
2. Plants of the new *Alstroemeria* and 'Tescreda Improved' differ slightly in flower color.
3. Plants of the new *Alstroemeria* have shorter flower pedicels than plants of 'Tescreda Improved'.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant. The photograph comprises a side perspective view of a typical flowering plant of 'Tesantarc' grown in a container.

DETAILED BOTANICAL DESCRIPTION

The aforementioned photograph and following observations and measurements describe plants of the new *Alstroemeria* grown during the winter and early spring in 4.6-liter containers in a glass-covered greenhouse in De Kwakel, The Netherlands. During the production of the plants, day and night temperatures averaged 12° C. and light levels averaged 7,000 lux. Plants were 22 weeks old when the photograph and description were taken. Color references are made to The Royal Horticultural Society Colour Chart, 2007 Edition, except where general terms of ordinary dictionary significance are used.

Botanical classification: *Alstroemeria hybrida* 'Tesantarc'.

Parentage:

*Female, or seed, parent*.—Proprietary selection of *Alstroemeria hybrida* identified as code number Pa6028x002, not patented.

*Male, or pollen, parent*.—Proprietary selection of *Alstroemeria hybrida* identified as code number Pb6903x035, not patented.

Propagation:

*Type*.—By rhizome divisions.

*Time to produce a rooted young plant, summer*.—About seven weeks at 20° C.

*Time to produce a rooted young plant, winter*.—About eight weeks at 16° C.

*Root description*.—Fibrous and fleshy; white in color.

*Rooting habit*.—Freely branching; medium density.

*Rhizome length*.—About 3.4 cm.

*Rhizome diameter*.—About 6 mm.

*Rhizome texture*.—Smooth.

*Rhizome color*.—Close to 195A to 195B.

Plant description:

*Plant and growth habit*.—Herbaceous perennial; upright, somewhat outwardly spreading and uniformly mounded plant habit; broad inverted triangle; freely branching habit with about 19 primary lateral branches developing per plant; relatively short internodes, dense and bushy appearance; sturdy and strong plant form; moderately vigorous growth habit.

*Plant height*.—About 24.3 cm.

*Plant diameter* (*area of spread*).—About 32.6 cm.

Lateral branch description:

*Aspect*.—Mostly upright to somewhat outwardly spreading.

*Length*.—About 11 cm.

*Diameter*.—About 8 mm.

*Internode length*.—About 8 mm.

*Strength*.—Moderately strong.

*Texture*.—Smooth, glabrous; waxy cuticle.

*Color*.—Close to 144B; waxy cuticle, close to 145A.

Foliage description:

*Arrangement*.—Alternate; below the peduncles in a single whorl; simple.

*Length*.—About 6.4 cm.

*Width*.—About 2.7 cm.

*Shape*.—Ovate; twisting.

*Apex*.—Acute.

*Base*.—Cuneate.

*Margin*.—Entire.

*Texture, upper and lower surfaces*.—Smooth, glabrous.

*Venation pattern*.—Parallel.

*Color*.—Developing leaves, upper surface: Facing downward, close to 143A. Developing leaves, lower surface: Facing upright, close to between 141B and 143A. Fully expanded leaves, upper surface: Facing downward, close to 137B; venation, close to 141A. Fully expanded leaves, lower surface: Facing upright, close to N137A to N137B; venation, close to 143A.

*Petioles*.—Length: About 2.6 cm. Diameter: About 2 mm by 7 mm. Color: Close to between 143A and 144A.

Flower description:

*Flower type and habit*.—Single zygomorphic flowers arranged in compound umbels; flowers face mostly outwardly to upright; perianth segments separate; freely flowering habit with about 16 flowers developing per inflorescence and about 300 flowers developing per plant.

*Natural flowering season*.—Plants begin flowering about eight weeks after planting; flowering continuous from summer into the autumn in The Netherlands.

*Fragrance*.—None detected.

*Flower longevity on the plant*.—About ten days; flowers not persistent.

*Flower buds*.—Length: About 3.7 cm. Diameter: About 1.5 cm. Shape: Obovate. Color: Close to 145B; distally, closer to 146A.

*Umbel height*.—About 11.4 cm.

*Umbel diameter*.—About 15 cm.

*Flower diameter* (*horizontal*).—About 7.1 cm.

*Flower length* (*vertical*).—About 7.4 cm.

*Flower depth* (*height*).—About 6.2 cm.

*Perianth*.—Arrangement: Six segments arranged in two whorls, each whorl with two lateral and one median segments. Size, inner perianth: Length, lateral segments: About 7.1 cm. Width, lateral segments: About 2.2 cm. Length, median segments: About 6.1 cm. Width, median segments: About 2.4 cm. Size, outer perianth: Length, lateral segments: About 6.5 cm. Width, lateral segments: About 3.5 cm. Length, median segments: About 7 cm. Width, median segments: About 3.5 cm. Shape, inner perianth, lateral and median segments: Oblanceolate. Shape, outer perianth, lateral and median segments: Flabellate. Apex, inner perianth, lateral and median segments: Abruptly acute. Apex, outer perianth, lateral and median segments: Emarginate with small abruptly acute apex. Base, inner perianth, lateral and median segments: Narrowly cuneate. Base, outer perianth, lateral and median segments: Long cuneate. Margin, inner perianth, lateral and median segments: Entire. Margin, outer perianth, lateral and median segments: Towards the apex, finely serrate; towards the base, entire. Texture, inner and outer perianths, lateral and median segments: Smooth, glabrous; slightly velvety. Color, inner perianth: When opening, lateral segments, upper surface: Close to 157D; towards the base, close to 157C; apex, close to 143B; narrowly elliptic-shaped spots, close to 178B. When opening, median segments, upper surface: Close to 157C to 157D; apex, close to 143C; narrowly elliptic-shaped spots, close to 178C. When opening, lateral segments, lower surface: Close to 157D; towards the base, close to 157B; apex, close to 143B; narrowly elliptic-shaped spots, close to 199D. When opening, median segments, lower surface: Close to 157C to 157D; apex, close to 143C; narrowly elliptic-shaped spots, close to 178C. Fully opened, lateral segments, upper surface: Close to NN155D; central blotch, close to 157D; apex, close to 143A; narrowly elliptic-shaped spots, close to 178A and 178B. Fully opened, median segments, upper surface: Close to NN155D; apex, close to 143A; narrowly elliptic-shaped spots, close to 176B to 176C. Fully opened, lateral segments, lower surface: Close to NN155C; light central blotch, close to 157D; apex, close to 143A; towards the base, tinged with close to 182D; narrowly elliptic-shaped spots, close to 197C. Fully opened, median segments, lower surface: Close to NN155D; apex, close to 143A; narrowly elliptic-shaped spots, close to 176B to 176C. Color, outer perianth: When opening, lateral and median segments, upper surface: Close to NN155C tinged with close to 69B; apex, close to 138B. When opening, lateral segments, lower surface: Close to NN155C tinged along the midvein with close to 70D; apex and midvein, close to 141A. When opening, median segment, lower surface: Close to NN155C heavily tinged along the midvein and towards the base with close to 70D; apex and midvein, close to 141A. Fully opened, lateral segments, upper surface: Close to NN155C to NN155D slightly tinged with close to 69C; apex, close to 143C. Fully opened, median segments, upper surface: Close to NN155C to NN155D tinged with close to 69C; apex, close to 143C. Fully opened, lateral segments, lower surface: Close to NN155C to NN155D tinged along the midvein and towards the apex with close to 67D; apex, close to 143A. Fully opened, median segments, lower surface: Close to NN155C to NN155D heavily tinged along the midvein and towards the apex with close to 67D; apex, close to 143A.

*Pedicels*.—Length: About 1.9 cm. Diameter: About 2.5 mm. Strength: Moderately strong. Angle: About 20° from vertical. Texture: Smooth, glabrous; waxy cuticle. Color, upper and lower surfaces: Close to 144B; waxy cuticle, close to 145A.

*Reproductive organs*.—Stamens: Quantity per flower: Six. Filament length: About 3.6 cm. Filament color: Close to 75A; towards the base, close to 145A. Anther shape: Double reniform. Anther length: About 4 mm. Anther color: Close to 148A to 148B. Pollen amount: Abundant. Pollen color: Close to 152A. Pistils: Quantity per flower: One. Pistil length: About 4.1 cm. Style length: About 3.4 cm. Style color: Close to 62B; towards the base, close to 145A. Stigma shape: Triparted; parts, club-shaped, curved. Stigma color: Close to N155B. Ovary color: Close to 146B.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain, high temperatures of about 35° C. and to be hardy to USDA Hardiness Zone 8.

It is claimed:

1. A new and distinct *Alstroemeria* plant named 'Tesantarc' as illustrated and described.

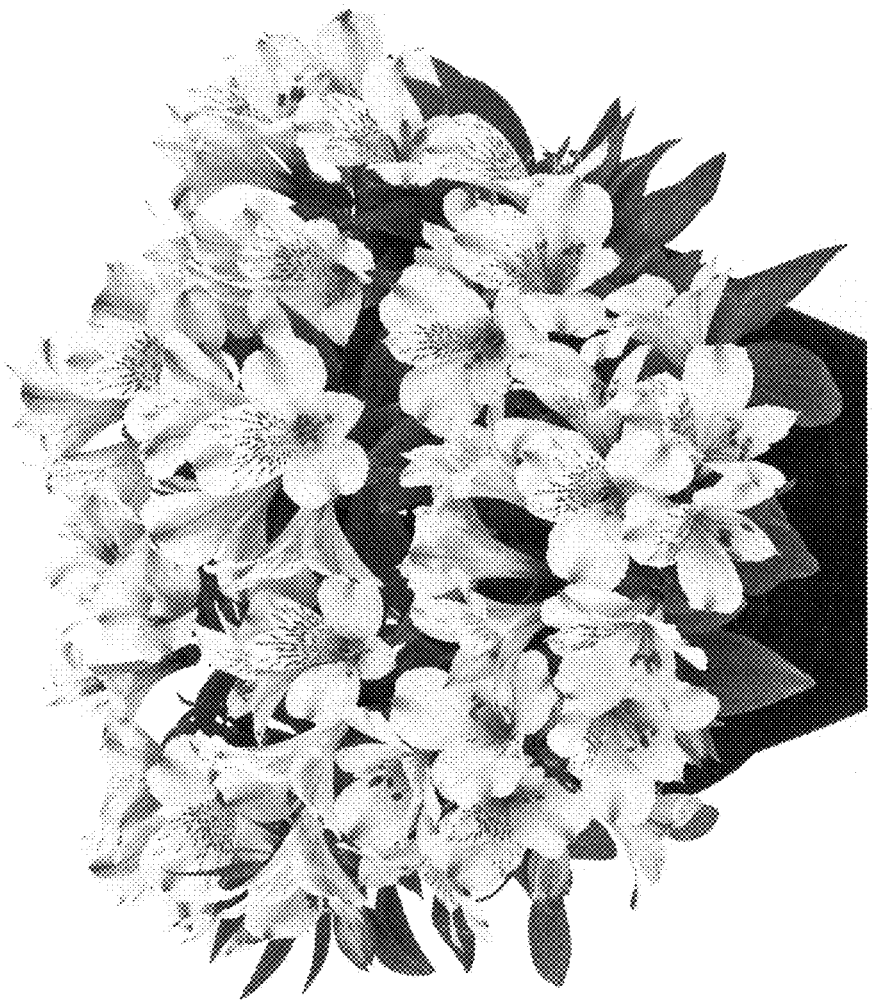

* * * * *